US00PP11833P2

(12) United States Plant Patent
Jessel, Jr.

(10) Patent No.: US PP11,833 P2
(45) Date of Patent: Apr. 3, 2001

(54) CARNATION PLANT NAMED 'CFPC DESIRE'

(75) Inventor: Walter H. Jessel, Jr., Gonzales, CA (US)

(73) Assignee: California Florida Plant Co, LP, Salinas, CA (US)

( * ) Notice: Subject to any disclaimer, the term of this patent is extended or adjusted under 35 U.S.C. 154(b) by 0 days.

(21) Appl. No.: 09/181,007

(22) Filed: Oct. 28, 1998

(51) Int. Cl.[7] ..... A01H 5/00
(52) U.S. Cl. ..... Plt./278
(58) Field of Search ..... Plt./278, 277, 282, Plt./283

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new variety of carnation plant producing burgundy flowers.

1 Drawing Sheet

BACKGROUND OF THE INVENTION

The present invention relates to a new and distinct variety of carnation plant which was discovered by me as a natural branch mutation in a controlled planting of 'CFPC Passion' (U.S. Plant Pat. No. 10,416). The varietal denomination of the new variety is 'CFPC Desire'.

SUMMARY OF THE INVENTION

Among the novel characteristics possessed by the new variety which distinguishes it is burgundy flowers. When grown under glass in 4½ inch plastic pots pinched plants are about 7¾ inches tall and about 7 inches diameter (average). Flower diameter is about 2 inches (average) with a ¾ inch crown (average). Foliage is about 3½ inches long and about 5/16 inches wide.

Asexual reproduction by propagation by cuttings of the new variety as performed in Salinas, Calif., shows that the foregoing and other distinguishing characteristics come true to form and are established and transmitted through succeeding propagations.

COMPARISON WITH PARENT

The new variety differs from its parent 'CFPC Passion', U.S. Plant Pat. No. 10,416, in flower color.

BRIEF DESCRIPTION OF ILLUSTRATION

The accompanying illustration shows typical specimens of the vegetative growth and flowers of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Color Chart (R.H.S.C.C.). The terminology used in color description herein refers to plate numbers in the aforementioned color chart. Phenotypical expression may vary depending upon environmental, seasonal and cultural conditions.

The information provided herein is based on observations of plants grown inside commercial greenhouses at Salinas, Calif. The height of plant and flower and foliage size are established as an average using standard commercial cultural practices.

Classification:
*Botanical.*—*Dianthus caryophyllus.*
*Commercial.*—Carnation, greenhouse type, suitable for production as a pot spray.

1. Plant:
*Height.*—About 7¾ inches.
*Growing habit.*—Herbaceous, semi-upright.
*Blooming habit.*—As a spray (pot).
*Blooming season.*—Year round.
*Rooting time.*—About 18 days.
*Disease resistance.*—Good, typical of carnations.

2. Foliage:
*Color.*—Upper side: Near 137A. Lower side: Near 137B.
*Size.*—About 3½ inches long, 5/16 inches wide.
*Quantity.*—Numerous.
*Shape.*—Lanceolate.
*Texture.*—Smooth.
*Ribs.*—Central, Keeled.
*Arrangement.*—Bi-lateral along stem.
*Stem color.*—Near 135B.
*Pedicel.*—Near 135B.

3. Bud:
*Shape.*—Ovoid.
*Color.*—Near 138B.
*Length.*—About 1 3/16 inches.
*Diameter.*—About 7/16 inch.

4. Calyx:
*Number of bracts.*—About 5.
*Length.*—About ¼ inch.
*Width.*—About 3/16 inch.
*Color.*—Outside — near 138B. Inside — near 145C.
*Bursting/Splitting.*—Has not been observed.

5. Bloom:
*Shape.*—Round.
*Size.*—Diameter average: About 2 inches. Depth average: About ¾inch.
*Borne.*—As a spray of about 2 to 3 blooms per spray.

*Color.*—General tonality: Wine red. Upper side: Near 60B. Lower side: Near 60C. Center: Near 60B. Outer petals: Near 60B.

*Fragrance.*—None to slight.

*Lastingness of bloom.*—About 1 week after cutting.

6. Petals:

*Number.*—About 16.

*Outer petals.*—Length: About 1⅔ inches. Width: About 13/16 inch.

*Central petals.*—Length: About 1⅓ inches. Width: About ¾ inch.

*Texture.*—Smooth.

*Form.*—Fan shaped.

*Appearance.*—Shiny.

*Margin.*—Smooth.

7. Reproductive organs:

*Stamens.*—None (male sterile).

*Pistil.*—Number: 1. Color: Whiter than 155D. Length: 1 inch.

*Stigma.*—Number: About 3. Color: Whiter than 155D.

*Ovary.*—Shape: Conical. Color: Base — Near 11D. Body — Near 144A. Apex — Near 144A.

*Fertility.*—Female: Good. Male: None.

I claim:

1. A new and distinct carnation plant of the variety substantially as shown and described.

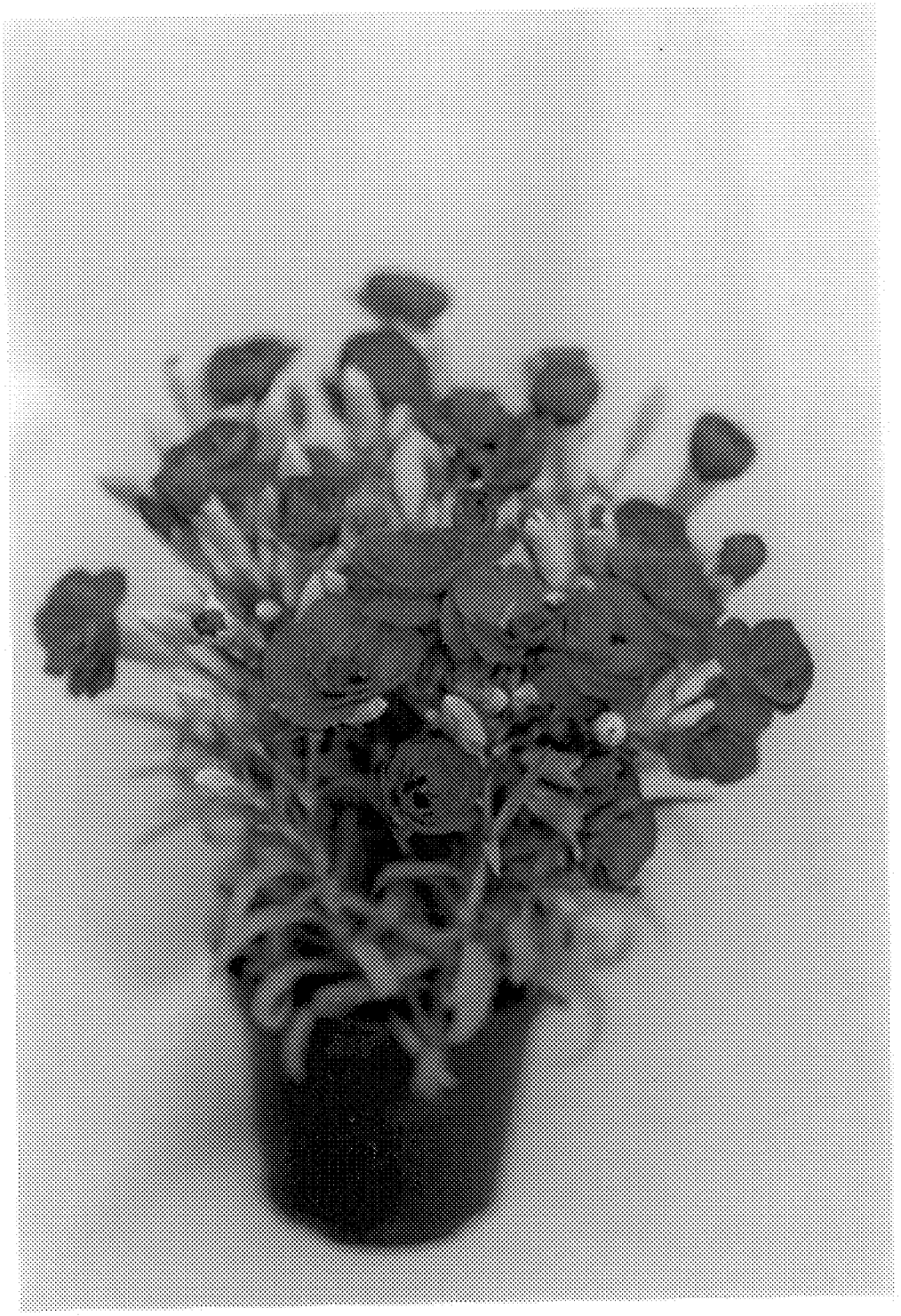

* * * * *